United States Patent [19]

Samuels et al.

[11] 4,204,526
[45] May 27, 1980

[54] ARTERIAL GRAFT AND PACKAGE

[76] Inventors: Peter B. Samuels, 14708 Sutton St., Sherman Oaks, Calif. 91403; Ernest Wood, 2465 Ivanhoe Dr., Los Angeles, Calif. 90039

[21] Appl. No.: 938,446

[22] Filed: Aug. 31, 1978

[51] Int. Cl.² ............................................. A61B 19/00
[52] U.S. Cl. ......................................... 128/1 R; 150/3
[58] Field of Search .............. 128/1 R, 334 R, 349 R; 3/1, 1.4; 206/363, 364, 438; 150/3; 229/62

[56] References Cited
U.S. PATENT DOCUMENTS
3,389,733  6/1968  Siegel ........................................ 150/3

OTHER PUBLICATIONS
"DeBakey ® Vasculour ®—D Arterial Grafts" USCI, A Division of C. R. Bard, Inc. Pamphlet—1973.

Primary Examiner—Willis Little
Attorney, Agent, or Firm—McDougall, Hersh & Scott

[57] ABSTRACT

An arterial graft forming package which includes an elongate graft forming porous base member housed within an elongate see-through bag of plastic material having an open end provided with releasable sealing means and finger loops on the outer walls of the bag adjacent the sealing means for disengagement of the sealing means and for holding the bag in open position during use.

5 Claims, 4 Drawing Figures

ARTERIAL GRAFT AND PACKAGE

This invention relates to an arterial graft and particularly to a device for use in the preparation of same.

In my co-pending application Ser. No. 739,650 filed Nov. 8, 1976 and entitled "Graft Forming Device", description is made of a graft forming device comprising an elongate porous base member housed within a rigid or flexible enclosure. The graft is prepared by the introduction of patient's blood into the interior of the enclosure for clotting onto the walls of the porous base member while the enclosure is sealed.

It is an object of this invention to provide an improvement whereby the construction of the enclosure is greatly simplified; the cost of the device is markedly reduced; ease of use of the device is greatly improved; and in which processing to form the graft can be converted to a one hand operation whereby the preparer has greater freedom and flexibility in the graft forming process while still being able to maintain aseptic conditions in preparing the graft for use.

Figure 1:
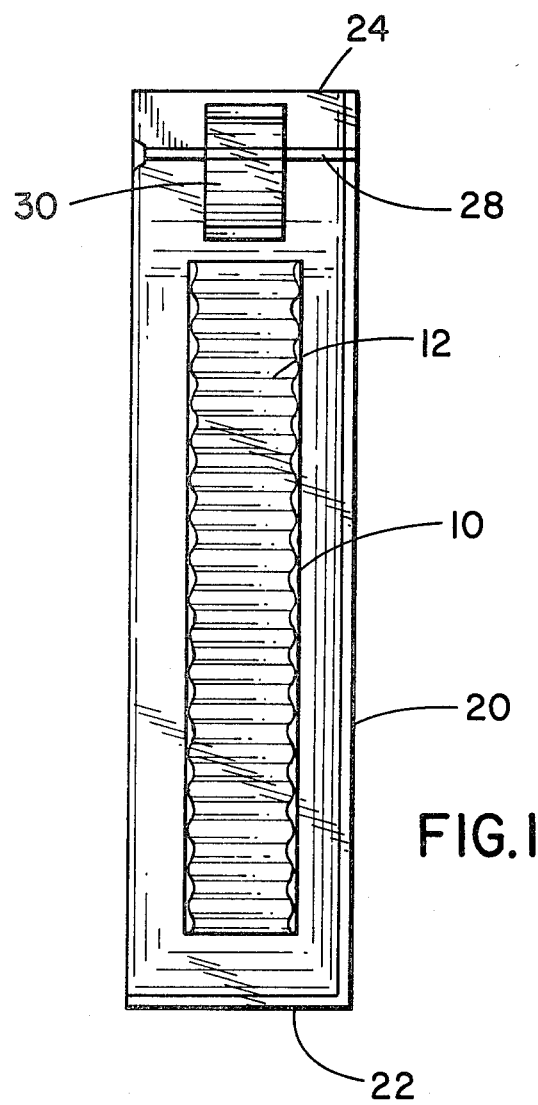
Figure 2:
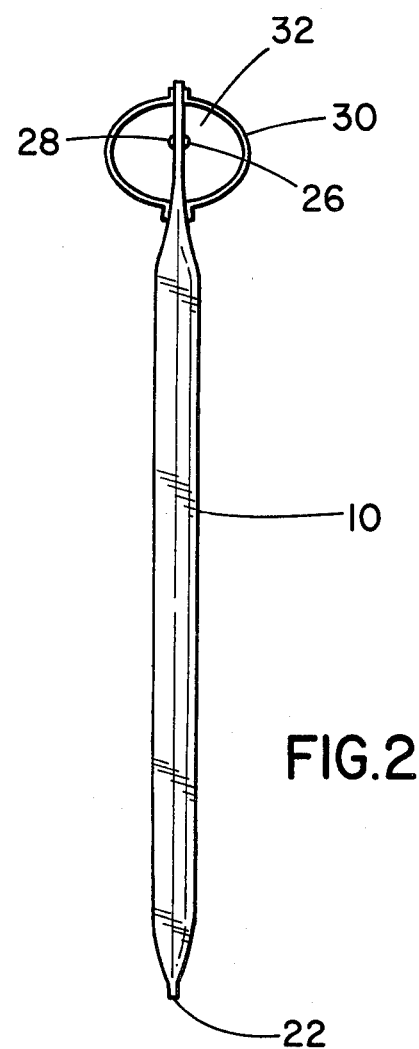
Figure 4:
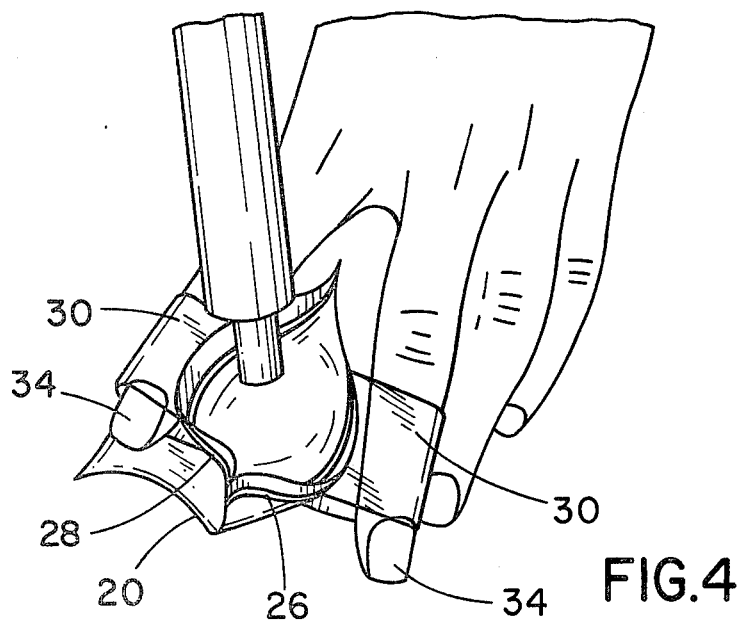
Figure 3:
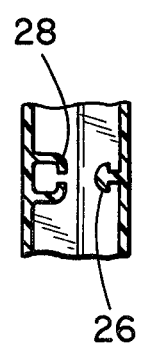

These and other objects and advantages of this invention will hereinafter appear and for purposes of illustration, but not of limitation, an embodiment of the invention is shown in the accompanying drawing in which FIG. 1 is a front elevational view of the graft forming device embodying the features of this invention, FIG. 2 is a side elevational view of the device shown in FIG. 1, FIG. 3 is an enlarged sectional view of the interlocking means for releasably sealing the open end of the bag, and FIG. 4 is a prospective view showing the manner in which the bag may be maintained in open position while inserting patient's blood.

As described in the aforementioned co-pending application, the graft is in the form of an elongate porous base member 10 of a woven or non-woven textile material formed of fibers such as mylar, dacron, rayon, cotton, silk and the like fibrous material. The base member 10 is in the form of an elongate member, preferably formed with corrugations 12 to provide for stretchability in the lengthwise direction and bendability in all directions while militating against collapse. The corrugations 12, which are generally in the form of longitudinally spaced circumferential ribs formed in the walls of the tubular base member 10, enable the base member to be stretched and bent in a manner to open the interstices of the porous fabric for better penetration by the blood and for more complete occlusion of the interstices during the clotting of the blood.

In the modification illustrated in FIG. 3 of the aforementioned application, the base member is housed within a chamber formed of a flexible, fluid impervious plastic film forming material, having an open end adapted to be sealed by a stopper having a pair of passages, one for penetration by a tubular member through which patient's blood is introduced into the chamber, and the other for venting the air displaced by the blood as it is introduced into the chamber.

In accordance with the practice of this invention, the chamber in which the porous base member 10 is packaged for grafting comprises an elongate tubular member 20 of a highly flexible fluid impervious film forming material, which is transluscent and preferably transparent so as to be able to see through into the interior thereof. Suitable material of which the chamber or bag may be formed include polyethylene, polypropylene, ethylene-propylene copolymer, ethylene-propylene polyene (EPDM) interpolymers, polybutadiene, and copolymers of butadiene with styrene, acrylate and the like plastic materials. The bag 20 can be formed by blow molding or, as illustrated in the drawing, the bag can be formed of a sheet of film plastic folded over and heat sealed along the free edges. One end 22 of the bag is closed as by heat sealing while the other end 24 is open to provide access to the interior of the bag. In the illustrated modification, the means for releasably sealing the open end of the bag comprises a tongue 26 which extends across the interior surface of one wall for interlock in sealing relation within a sealing groove 28 across the interior surface of the facing wall. Instead of an interlocking tongue and groove arrangement, use can be made of other conventional means for closure of the open end of the bag in sealing engagement, such as pressure sensitive adhesive means selected to be inert to blood or other aqueous medium.

In accordance with the practice of this invention, means are provided as a part of the bag for displacement of the walls in the direction away from each other to open the bag for access to the interior thereof and for holding the bag open while blood is introduced for use in preparing the graft. Such means comprises finger loops 30 or tabs on each of the opposite sides of the bag adjacent the open end. In the illustrated modification such finger loops or tabs are formed of strips of material secured at their upper ends to a portion of the outer walls of the bag at a level at or above the interlocking members while the lower end portions are secured at or below the level of the interlocking porous members with the strips being dimensioned to have a length greater than the distance between the points of attachment of their upper and lower ends so as to provide a loop portion 30 therebetween.

Such strips can be of the same material as that of which the bag is formed whereby the ends of the strips can be secured to the bag as by heat sealing, or the strips can be formed of other material such as tapes, cord, ribbon or the like fixed to the outer walls of the bag as by heat sealing, adhesive, clips, stitching or the like. It is preferred to make use of a means for joinder that does not penetrate the walls of the bag so as to avoid possible penetration of contaminants into the interior of the bag when the open end is sealed by the interlocking means.

In use, the base member 10 is packaged in the bag 20 with the end sealed to enclose the base member in sealing relation. In this condition, the base member can be sterilized or the entire assembly sterilized for shipment to distant stations for use in sterilized condition.

When it is desired to form the graft, the bag is opened by application of force by pulling the finger loops or tabs in the direction away from each other. This can conveniently be done by inserting the index finger of each hand into the opposing loops and applying a pull sufficient to dislodge the tongue from the groove or otherwise disengage the sealing means. The bag can thus be held open with the index finger and thumb of one hand and blood can be introduced into the interior of the bag through the open end, as illustrated in FIG. 4.

While the bag is still held in open position between the fingers and after the blood has been introduced, the bag can be squeezed with the other hand for at least partial displacement of air, after which the open end of the bag can be resealed via the interlock. By massaging the graft, as described in the aforementioned co-pending application, the blood will be distributed for coating the walls of the base member.

Thereafter the unit can be set aside until it is desired to make use of the prepared graft. At such time, the end of the bag can be reopened in the manner described to provide access to the prepared graft for removal and use.

It will be apparent that during the packaging, storage and shipment, except for the period of time that the bag is open for the introduction of the patient's blood, the graft forming member and the graft prepared therefrom are maintained under aseptic conditions within the sealed bag.

It will be apparent that I have provided an inexpensive and efficient graft forming device which is simple in construction and easy in operation and which can be handled even by inexperienced personnel to produce a graft.

It will be understood that changes can be made in the details of construction, arrangement and operation without departing from the spirit of the invention, especially as described in the following claims.

We claim:

1. An arterial graft forming package comprising an elongate graft forming porous base member and an elongate bag containing the graft forming base member therein, said bag being formed of a fluid impervious, flexible plastic which is inert to blood and sealed all around except for an access opening at one end, sealing means adjacent the open end capable of relative lateral movement between closed sealing connection and open position, finger loops secured to the opposite outer walls of the bag adjacent the open end to enable the insertion of fingers of one hand for finger engagement to apply force in the direction away from each other for disengagement of the sealing connection and for holding the end of the bag in open position with one hand, leaving the other hand free.

2. An arterial graft forming package as claimed in claim 1 in which the tabs comprise strip members secured at their opposite ends to portions above and below the sealing means respectively and in which the strip members are dimensioned to have a length greater than the distance between the opposite secured end to define a finger loop in between.

3. An arterial graft forming package as claimed in claim 1 in which the graft forming base member is formed of a textile material.

4. An arterial graft forming package as claimed in claim 1 in which the graft forming base member is corrugated substantially throughout its length to provide for lengthwise stretching movement and for bending movement in all directions while preventing collapse of the base member in use.

5. An arterial graft forming package comprising an elongate graft forming porous base member and an elongate bag containing the graft forming base member therein, said bag being formed of a fluid impervious, flexible plastic which is inert to blood and sealed all around except for an access opening at one end, sealing means adjacent the open end capable of relative lateral movement between closed sealing connection and open position, tabs secured to the opposite outer walls of the bag adjacent the open end for finger engagement to apply force in the direction away from each other for disengagement of the sealing connection and for holding the end of the bag in open position in which the graft forming base member is a plastic material having porous walls.

* * * * *